United States Patent [19]

Fixel

[11] 4,180,873
[45] Jan. 1, 1980

[54] IMPLANTED ACETABULAR PROSTHESIS

[76] Inventor: Irving E. Fixel, 111 N. 31 Ave., Hollywood, Fla. 33021

[21] Appl. No.: 748,233

[22] Filed: Dec. 6, 1976

[51] Int. Cl.² ............................................. A61F 1/24
[52] U.S. Cl. ...................................... 3/1.912; 3/1.91; 128/92 C
[58] Field of Search ............................... 3/1.91–1.913, 3/1; 128/92 C, 92 CA

[56] References Cited
U.S. PATENT DOCUMENTS

| 3,894,297 | 7/1975 | Mittelmeier et al. | 3/1.912 |
| 3,924,275 | 12/1975 | Heimke et al. | 3/1.912 |

FOREIGN PATENT DOCUMENTS

| 1047640 | 7/1953 | France | 128/92 C |
| 1122634 | 5/1956 | France | 128/92 C |
| 278022 | 11/1970 | U.S.S.R. | 3/1.912 |

Primary Examiner—Ronald L. Frinks
Attorney, Agent, or Firm—Richard M. Saccocio

[57] ABSTRACT

A prosthetic device for repairing or replacing joints of skeletal bones such as the acetabulum is attached in a new manner by a force fit in the prepared bone void of the acetabulum. The prosthetic device includes a frusto-conical shaped hollow cup which is force fitted into the prepared bone void and carries a stop flange to prevent further penetration of the bone void. A hollow plastic liner is housed within the cup.

3 Claims, 1 Drawing Figure

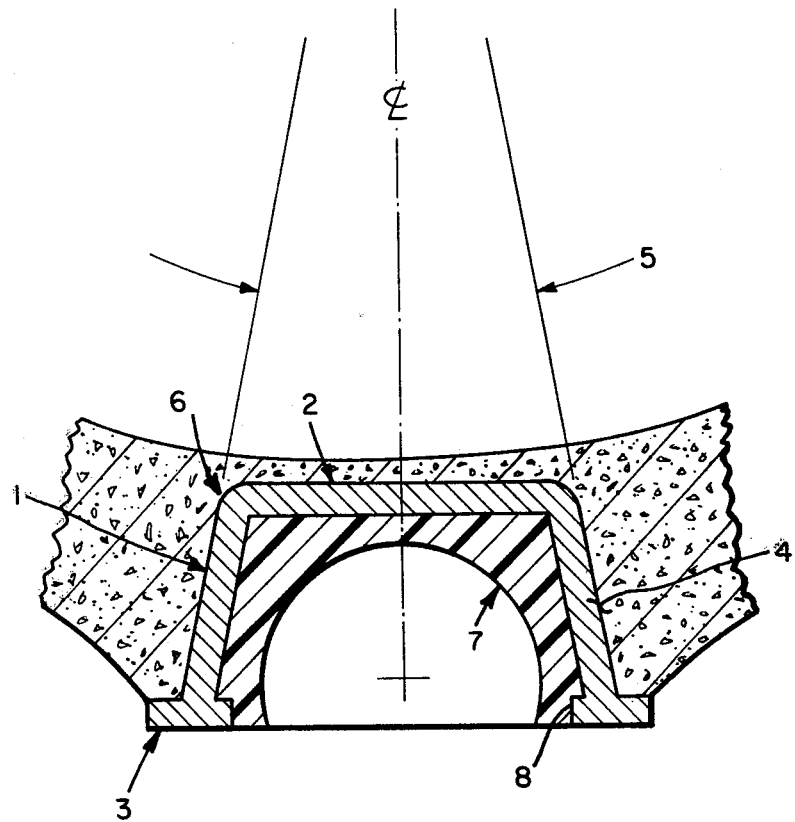

IMPLANTED ACETABULAR PROSTHESIS

BACKGROUND OF THE INVENTION

1. Field of the Invention.

This invention involves an implantable prosthetic device to substitute certain areas of the skeletal bones in the human body such as the acetabulum or parts of other freely movable joints.

2. Description of Prior Art.

There are many types of prosthetic devices designed to fit the void of a diseased or damaged acetabulum or the void portion of the hip joint. This invention deals with the prosthetic component commonly referred to as the acetabular cup. In most cases the acetabular cup is inserted into a bone cavity either by using cements or by utilizing sharp edges, such as serrations or other irregularities on the outer surface of the implant to serve as anchoring means. Most implants have spherical or cylindrical cross sections. By using these implants, a number of problems are encountered such as loosening of the component and a subsequent displacement which may lead to a total failure. Also in many cases there is too much free space between the cup and the bone cavity resulting in a void which causes undesired stress concentrations. Often an application of a great amount of cement is applied to attempt to minimize this effect.

BRIEF DESCRIPTION OF THE INVENTION

The scope of this invention is to disclose reliable anchoring of an implanted acetabular component. It is also an object of this invention to avoid dangerous stresses applied to the bone.

Another object of this invention is to provide accurate means to be able to accomplish successful implantation lending lasting stability to the prosthesis.

BRIEF DESCRIPTION OF THE DRAWINGS

In the single FIGURE, a cross-sectional view of the inventive acetabular cup is shown, as it is fitted to an acetabulum.

DETAILED DESCRIPTION OF THE PREFERRED EMBODIMENT

The improved acetabular component described here and also presented on the attached drawing is composed of the following:

The outer shell of the prosthesis is the acetabular cup 1. This cup has a frustro-conically shaped body with circular crossections. The narrow end of this cup is enclosed by a flat cover 2. This cover 2 is an integral part of the cup 1. The larger end of the frustro-conical body incorporates a circlar flange 3 constituting means to stop the implant from further penetration into the acetabulum under load. The drawing also shows the crossectional view of the modified acetabular cavity 4. The modification is done through reaming or by using precision machine tools to enlarge the acetabular cavity 4 in order to fit the cup 1 and the adjacent edges of the flange 3 into said cavity 4. The included angle of the taper 5, defined by the edges of the frustro-conical cup 1, and angle of the void, defined by the reamed inside edges of the acetabular cavity 4, are identical angles. The crossectional size of the reamed hole in the cavity is smaller than the crossectional size of the cup 1 by a very small amount. The included angle of the taper 5 is a very small angle typically in order of 1 to 2 degrees. By pressing the cup 1 into the cavity 4 to reach a position as shown in the drawings, substantial stresses will be created which at the interface between the frustro-conical surfaces of the cup 1 and that of the cavity 4. Said stresses compress the cup 1 and as a result, substantial forces will clamp the cup 1 anchoring it into the cavity 4. This will also create a great deal of frictional forces equally distributed along the affected surface areas, resisting both rotational as well as axial or radial displacement of the implant. The implant may be removed only by forceful means. Both the flange 3 and the cover 2 rest flush against the flat machined areas of the bone surfaces of the cavity 4 stopping the prosthesis in its final position after being impacted. Within cup 1 is a molded plastic liner 7 with a low co-efficient of friction having a frustro-conical outer surface and a hemispheric inside cavity designed to accept a ball shaped component as part of another joining prosthesis. Liner 7 also acts as an artificial cartilage of the joint. Said liner 7 is press-fitted into the cup 1 and held securely in place by a circular rim 8 wich is part of the cup 1. The invention shown and described herein is considered to be a practical and preferred embodiment. It is recognized, however, that departures made therefrom are within the scope of the invention and that obvious modifications will occur to a person skilled in the art.

What I claim is:

1. A prosthetic device for repair or replacement of joints of skeletal bones by implantation in skeletal bone, said prosthetic device comprising
   a hollow cup member having a small end and a large end, said cup having substantially smooth inner and outer surfaces, said outer surface having a frustro-conical shape and a size which is adapted to effectuate a force fit relationship with a matching frustro-conically shaped void in skeletal bone,
   a liner positioned within said cup member having an inner surface approximating a hemispherical void and a substantially smooth outer surface, said outer surface being in contact with said inner surface of said cup,
   means attached to said cup adapted to prevent said cup from further penetration into the void in the skeletal bone comprising a flange attached to said large end of said cup extending radially outward of said outer surface of said cup and a substantially flat cover attached to said small end of said cup.

2. The prosthetic device of claim 1, wherein the axial distance between corresponding surfaces of said flange and said cover is adapted to cause said cover and said flange to bear simultaneously against contacting surfaces of a void in skeletal bone and to limit a force fit relationship between said cup and the skeletal bone.

3. The prosthetic device of claim 1, including means attached to said cup to captively retain said liner within said cup said means comprising a flange attached to said cup at its large end said flange extending radially inward of said inner wall of said cup.

* * * * *